United States Patent [19]

Sasaki et al.

[11] 4,218,321
[45] Aug. 19, 1980

[54] DEVICE FOR REMOVAL OF EXCESS WATER FROM BLOOD

[75] Inventors: Kanji Sasaki; Tetsuro Suehiro; Akira Okada, all of Yokohama, Japan

[73] Assignees: Agency of Industrial Science & Technology; Ministry of International Trade & Industry, both of Tokyo, Japan

[21] Appl. No.: 930,159

[22] Filed: Aug. 2, 1978

[30] Foreign Application Priority Data

Aug. 5, 1977 [JP] Japan .................. 52-93995

[51] Int. Cl.$^2$ ...................... B01D 31/00; B01D 15/00
[52] U.S. Cl. .................... 210/259; 210/266; 210/283; 210/295; 210/321 B
[58] Field of Search ....... 210/321 B, 321 A, DIG. 23, 210/317, 259, 22, 23 R, 39, 283, 284, 287, 291, 321 R, 27, 295, 266, 500 M

[56] References Cited

U.S. PATENT DOCUMENTS

| | | | |
|---|---|---|---|
| 3,352,779 | 11/1967 | Austin et al. | 210/23 F |
| 3,525,686 | 8/1970 | Roberts | 210/22 |
| 3,560,380 | 2/1971 | Stade | 210/22 |
| 3,585,131 | 6/1971 | Esmond | 210/321 B |
| 3,608,729 | 9/1971 | Haselden | 210/321 B |
| 3,725,113 | 4/1973 | Chang | 117/82 |
| 3,827,565 | 8/1974 | Matsumura | 210/321 B |
| 3,865,726 | 2/1975 | Chibata et al. | 210/152 |
| 3,894,954 | 7/1975 | Serur | 210/321 B |
| 3,962,075 | 6/1976 | Fialkoff et al. | 210/22 A |
| 3,990,973 | 11/1976 | Boag et al. | 210/321 B |
| 4,013,564 | 3/1977 | Nose | 210/434 |
| 4,048,064 | 9/1977 | Clark | 210/23 R |

FOREIGN PATENT DOCUMENTS 565668  8/1977  U.S.S.R. ................ 210/321 B

OTHER PUBLICATIONS

"Characterization of a 1100–1300 M.W. Uremic Neurotoxin", Fenck–Brentano et al., Trns. Am. Soc. Art. Orgns., 1976, vol. 22, p. 163.

Primary Examiner—Benoît Castel
Assistant Examiner—David R. Sadowski
Attorney, Agent, or Firm—Oblon, Fisher, Spivak, McClelland & Maier

[57] ABSTRACT

A device for removal of excess water from blood is formed by having a plurality of solution chambers and a plurality of blood chambers arranged alternately, partitioning the adjoining ones of the alternately disposed chambers by insertion of semi-permeable membranes one each along the boundaries thereof and having a sorbent retained in the form of a bed inside the blood chambers, whereby the blood containing waste material and excess water in consequence of renal insufficiency is freed from such fouling substances by causing the blood to flow through the blood chambers in order for the beds of sorbent to deprive the blood of the waste material through sorption and for the high concentration solutions flowing through the adjoining solution chambers to deprive the blood of the excess water through osmosis effected through the medium of the semi-permeable membranes.

6 Claims, 5 Drawing Figures

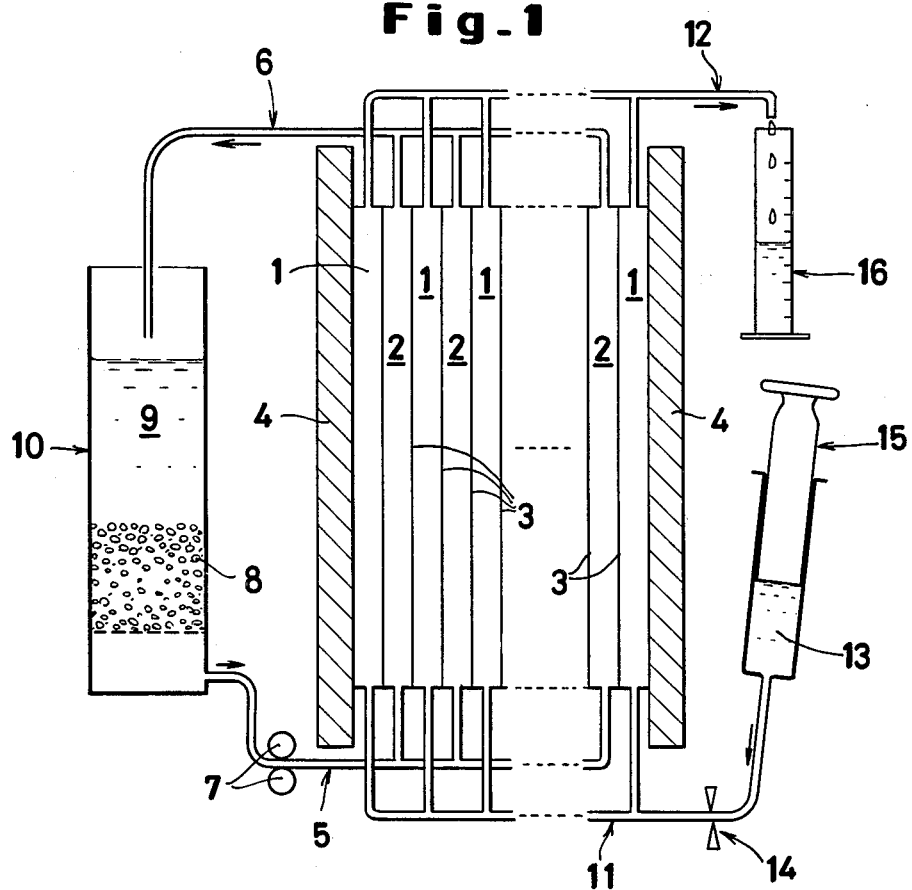
Fig_1
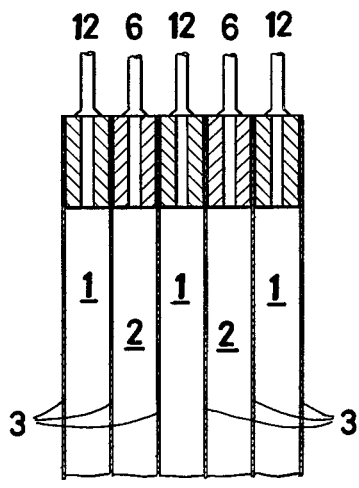
Fig_2
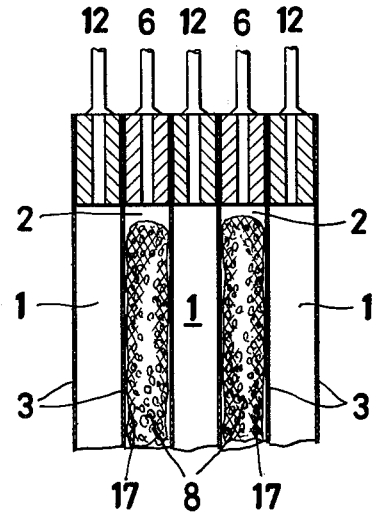
Fig_3

DEVICE FOR REMOVAL OF EXCESS WATER FROM BLOOD

BACKGROUND OF THE INVENTION

This invention relates to a for removal of excess water from blood in patients suffering from renal insufficiency.

Patients of chronic renal insufficiency are required to receive two to three hemodialytic treatments per every week. The devices employed today for hemodialysis generally require as much as 30 to 70 liters or even more of dialysate per treatment so that the overall systems for the treatment are quite large. As these systems are indispensable for sufferers of renal insufficiently, the inconveniences experienced in connection with such huge systems have urged development of a compact hemodialysis device designed to be carried on the patient's person. To this end, there has been developed a hemodializer miniaturized enough to make an artificial kidney device wearable (W. J. Kolff "Exponential Growth and Future of Artificial Organs" Artificial Organs, Vol. 1, 8-12, 1977, F. W. Markley et al "A New High Performance, Miniature Hemodializer" Trans. Amer. Soc. Artif. Int. Organs, Vol. 22, 612-617, 1976). There has also been proposed a method for decreasing the amount of dialysate required for the treatment by recycling the used dialysate via a special unit designed to purify and regenerate the used dialysate (A. Gordon et. al "Clinical maintenance hemodialysis with a sorbent-based low-volume dialysate regeneration system" Trans. Amer. Soc. Artif. Int. Organs, Vol. 17, 253, 1971). There has further been perfected a method for direct hemoperfusion which is effected not by use of any membrane but by virtue of the contact of the blood with an activated carbon sorbent coated with a permeable high polymer membrane formulated to preclude possible fragmentation of carbon dust (Chang T.M.S. et al "ACAC Microcapsule artificial kidney for long term and short term management of eleven patients with chronic renal failure" Trans. Amer. Soc. Artif. Int. Organs, Vol. 18, 465, 1972, J. D. Andrade et al "Coated Adsorbents for Direct Blood perfusion" Trans. Amer. Soc. Artif. Int. Organs, Vol. 18 473–484, 1972). Even with the wearable miniaturized hemodialysis device, at least 1.5 liters or so of dialysate is needed. It is considered fairly difficult to decrease the amount of the dialysate thus required any further. The method for direct hemoperfusion is capable of removing waste material from the blood and yet is incapable of removing excess water. Thus, this method requires the blood to undergo an additional treatment such as by ultrafiltration for the removal of the remaining excess water.

The methods adopted today for hemodialysis effectively accomplish the removal of excess water from the blood by utilizing the osmotic flow of water caused between the dialysate and the blood by increasing the concentration of the dialysate as well as the ultrafiltration caused by the differential pressure between the blood and the dialysate used as its motive power. Since, in this case, there is entailed the problem of equilibrium of osmotic pressure between the blood and the dialysate, the concentration of the dialysate is limited to the maximum of 400 m.Osm/liter in osmolarity. (S. Mendelssohn et al "High Glucose Concentration Dialysate in Chronic Hemodialysis" Trans. Amer. Soc. Artif. Int. Organs, Vol. 13, 249-253, 1967) The membrane generally used for hemodialysis has high solute permeability as well as high water flux. When the dialysate in use has a high concentration compared with the blood, therefore, there is a possibility that the solute of the dialysate will pass into the blood even to the extent of causing an abnormal rise in the osmotic pressure of the blood.

An object of the present invention is to provide a device for removal of excess water from blood which is capable of removing the waste material from the blood and, at the same time, removing the excess water from the blood.

Another object of this invention is to provide a device for removing excess water from blood which effectively operates with an extremely small amount of high concentration solution.

SUMMARY OF THE INVENTION

To accomplish the objects described above according to the present invention, there is provided a device for removal of excess water from blood which comprises a plurality of solution chambers filled with high concentration solution and a plurality of blood chambers adapted to permit flow of the blood subjected to perfusion, with the solution chambers and the blood chambers alternately arranged, and semi-permeable membranes possessing moderate water flux and negligibly low solute permeability and inserted one each along the boundaries of the adjoining ones of the alternately disposed chambers, whereby the blood is held in indirect contact with the high concentration solution through the medium of the semi-permeable membranes so that the excess water alone is permitted to pass to the dialysate side through osmosis and the solute is not permitted to pass to the blood side.

Further, either before or after its contact with the high concentration solution, the blood is sent through a sorbent to be deprived of the waste material through sorption. When the sorbent is enclosed with a material excelling in perviousness to liquids and the enclosed sorbent is retained inside the blood chambers, the removal of the waste material by sorption can be effected simultaneously with the removal of water. Since the construction contemplated by this invention permits a notable dimensional reduction in the solution chambers and the blood chambers, the overall amount of the dialysate used in the device can be decreased to a remarkable extent. If the semi-permeable membranes, while in the course of manufacture, are caused to incorporate therein substances essential to living organisms such as, for example calcium, glucose and essential amino acids, they serve the purpose of furnishing human systems with such valuable substances as well as the original purpose of removal of excess water from blood.

The other objects and characteristic features of the present invention will become apparent from the description to be given in further detail hereinafter with reference to the accompanying drawing.

BRIEF EXPLANATION OF THE DRAWING

FIG. 1 is an explanatory diagram illustrating one embodiment of the combination sorption and water removal device of the present invention.

FIG. 2 is an enlarged, partially sectioned view showing the positional relationship of the high concentration solution chambers, the blood chambers and the semipermeable membranes in the device of FIG. 1.

FIG. 3 is a partially enlarged view showing another preferred embodiment of the device of the present invention for removal of excess water from blood.

DESCRIPTION OF THE PREFERRED EMBODIMENT

Figure 4:
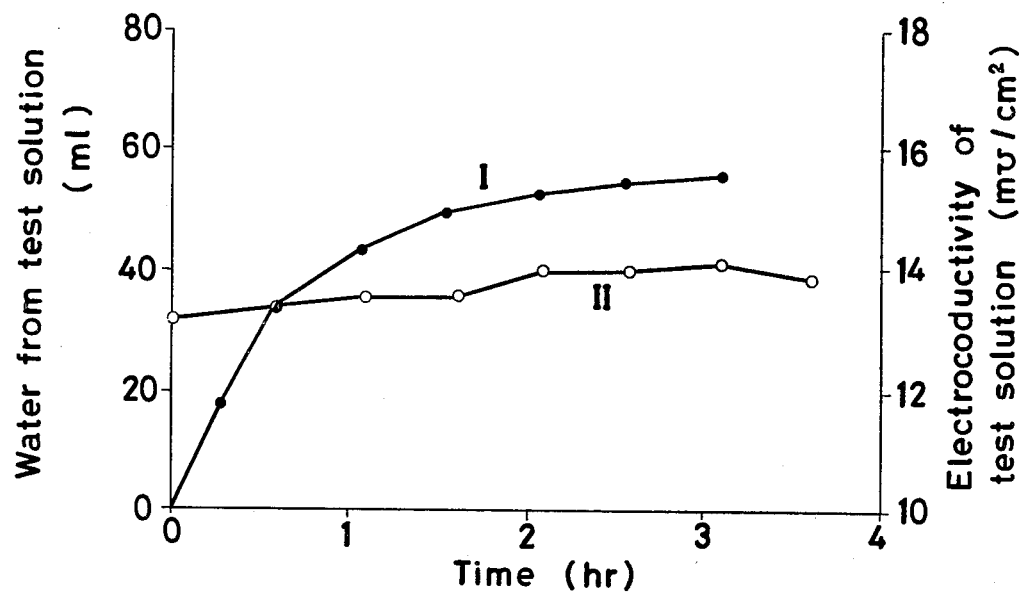
FIG. 4 and FIG. 5 are graphs showing the time-course changes of electroconductivity of the test solution and the amount of removed water from the test solution which were determined by the operation of the device of this invention.

The device for removal of excess water from blood according to the present invention will be described by reference to the illustrated preferred embodiment.

With reference to FIG. 1, the plurality of high concentration solution chambers 1 and the plurality of blood chambers 2 are alternately disposed and the adjoining ones of these chambers are partitioned by the semi-permeable membranes 3 inserted one each along the boundaries thereof. The individual solution chambers 1 and blood chambers 2 are formed to be liquid tight. The plurality of solution chambers 1 and the plurality of blood chambers 2 which are alternately arranged after the manner of a multi-layer sandwiches are integrally held in position between the opposite frames 4, 4'. The lower ends of the individual solution chambers 1 are connected to a solution inlet tube 11 which is connected at the other end to a syringe 15 filled with high concentration solution 13. The upper ends of the individual solution chambers 1 are connected to a solution outlet tube 12 which is connected at the other end to a measuring cylinder 16 designed to receive the waste solution and measure its volume. A blood inlet tube 5 is connected to the lower ends of the individual blood chambers 2 and a blood outlet tube 6 to the upper ends of the blood chambers respectively. When the device of this invention is actually used on a patient, the terminals of the inlet and outlet tubes are to be connected to appropriate arterial and venous cannulae at the patient, for example, to such cannulae in the arms. In the case of the experimental device under discussion, these terminals are connected to the blood container 10 containing the test solution. The test solution 9 in the blood container 10 is forwarded by the pump 7 to the individual blood chambers 2 via the inlet tube 5. The blood departing from the blood chambers 2 is returned via the outlet tube 6 to the blood container 10. In the case of the present embodiment, a bed of activated carbon 8 is formed inside the blood container to serve the purpose of removing waste material from the blood.

In the hemoperfusion device of the construction described above, the high concentration solution 13 in the syringe 15 is fed via the pinch cock 14 to the individual solution chambers 1. The pinch cock 14 is closed when all the solution chambers come to be filled to capacity with the solution.

Although the composition of the high concentration solution to be used for this invention depends on medical prescriptions, it must at least satisfy the minimum requirement of possessing high osmotic pressure. Examples of such solutions which are used today include dense solutions formulated for hemodialysis and solutions obtained by diluting such dense solutions to two to three times the original volumes. It is preferable that the dense solutions formulated for hemodialysis have a composition composed preponderantly of sodium chloride, sodium acetate and glucose or a composition composed preponderantly of calcium chloride and glucose.

High concentration solutions specially formulated as described below may also be used. Where the semi-permeable membranes in use have a very large area and the treatment for water removal from blood is required to be given for a long time, it is not improbable that a slight degree of ion permeability of the semi-permeable membranes can increase the ionic concentration in the blood to a degree more than is required. To preclude this undesired possibility, the ionic solute content of the solution is minimized and grape sugar, sucrose or some essential amino acid is added as a substitute solute. Inversely by taking advantage of the slight ion permeability of the semi-permeable membranes, a component lacking in the patient's blood such as, for example, calcium can be replenished by having that particular component incorporated in the high concentration solution formulated for use in the hemoperfusion.

To the individual blood chambers 2, the patient's blood is delivered at a prescribed flow rate through the blood inlet tube 5. For collection and supply of the blood, there may be used any of known means. The higher the concentration of these solutions used, in general, the higher the osmotic flow of water in the blood.

The blood in the blood chambers 2 comes into indirect contact with the high concentration solution in the solution chambers 1 through the medium of semi-permeable membranes 3. The semi-permeable membranes to be used for the present invention are not required to possess high water flux but are required to possess a very low solute permeability. To be specific, it is advantageous to use semi-permeable membranes possessing water flux in the range of from $2 \times 10^{-4}$ to $9 \times 10^{-4}$ ml/cm$^2$/min. and solute permeability in the range of from $1 \times 10^{-7}$ to $7 \times 10^{-6}$ cm/min.

Chiefly normal osmotic membranes made of acetyl cellulose with a high acetyl content are advantageously used as semi-permeable membranes. Besides these, membranes made of other cellulose derivatives having a low moisture content, aromatic polyamides such as polyphenylene terephthalamide, aromatic heterocyclic heat-resistant polymers such as polybenzimidazole, acrylonitrile copolymers and polypropylene copolymers having hygroscopic monomers graft polymerized thereto in small amounts are also usable.

When such semi-permeable membranes are used, the osmotic pressure and ionic concentration of the blood can be maintained substantially constant even if there is used a solution of high concentration approximating that of a saturated solution.

Generally the overall area of such semi-permeable membranes is determined by the rate at which the removal of water is required to be effected (the kidneys in normal state are said to excrete urine at an approximate rate of 1 to 2 ml/min) and the water flux of the membranes in use. In the device of this invention, the available area of the membranes can easily be adjusted by the unit size and number of the individual solution chambers and blood chambers. As concerns the shape, the membranes may be of a parallel plane type, a coiled type or hollow fiber type.

The thickness of the semi-permeable membranes is generally on the order of 10 $\mu$m. The unit length and unit width of the solution chambers and blood chambers can freely be fixed. The unit thickness of these chambers is in the range of from 150 to 500 $\mu$m. Where the blood chambers are desired to contain the sorbent, it is proper to give them a unit thickness of about 1 mm.

The overall area of the semi-permeable membranes available for contact with liquids can be increased and the volumes of the blood and the high concentration solution to be used can be notably decreased by designing the chambers in approximate dimensions.

When the blood flowing through the blood chambers comes into indirect contact with the high concentration solution through the medium of semi-permeable membranes, the excess water present in the blood passes into the solution. The ends of the solution chambers at which the chambers communicate with the outlet pipes 12 are constantly kept open so that whenever there is an increase in the volume of the solution owing to the transfer of excess water, the volume of solution thus increased will be allowed to flow into the measuring cylinder 16. This means that possible rupture of the semi-permeable membranes due to the osmotic pressure otherwise suffered to build up between the blood and the solution can be avoided.

When the high concentration solution has its water permeability degraded to a certain extent, the syringe 15 is operated to replace the exhausted solution in the solution chambers with a fresh supply of the solution, with the water permeability restored. This replacement of the solution can of course be effected by using a pump instead of the syringe.

The blood which has been given required perfusion through the indirect contact with the high concentration solution as described above is returned to the blood container 10. In the actual use of the device, this purified blood is returned to the human system.

For the removal of excess water, the blood may be treated in advance with a sorbent. Alternatively, the sorbent may be placed inside the blood chambers so that the blood, while flowing through the blood chambers, undergoes treatment with the sorbent at the same time that it is treated by the indirect contact with the high concentration solution. Otherwise, the treatment of the blood with the sorbent may be carried out after the blood has been freed from the excess water by the indirect contact with the solution.

In the device illustrated in FIG. 1, therefore, a bed of sorbent 8 is placed inside the model blood container 10. Actually, the sorbent may be placed at any point of the entire length of the blood inlet tube 5 or blood outlet tube 6. Otherwise, the sorbent may be wrapped up with a material 17 highly previous to liquids such as, for example, gauze and retained inside the blood chambers.

The sorbent to be used for this invention is required to be capable of sorbing sodium, potassium, magnesium, chlorine, urea, creatinine, uric acid and nitrogenous waste materials. Concrete examples of such sorbents include spheres of activated carbon, fibrous activated carbon which have been given a surface treatment so as to avoid inducing undesirable phenomena such as hemolysis, obstruction to blood flow. Medically tolerable complex compounds and chelate compounds are also used as the sorbents. The amount of the sorbent to be used in the device of this invention is suitable in the range of from 200 to 300 g (as activated carbon) for about 5 liters of the blood.

As is clear from the foregoing description, the hemoperfusion device of the present invention causes the blood to come into contact with the high concentration solution through the medium of semi-permeable membranes possessing moderate water flux and negligibly small solution permeability, so that the excess water alone is permitted to pass into the high concentration solution and virtually no solute is allowed to pass into the blood. Thus, there is no possibility of the osmotic pressure of the blood being heightened in consequence of the treatment.

The amount of the high concentration solutions required for the device is extremely small because the solution chambers and the blood chambers can be designed in very small dimensions. Since the solution can easily be replaced with a fresh supply without interruption of the treatment in progress, the treatment can be continuously performed without any degradation of the water permeability of the solution.

Further since the sorbent serving to remove the waste material from the blood by sorption can be retained inside the blood chambers, the device can be miniaturized enough for the patient to carry it on his person.

Now, the present invention will be described with reference to working examples of the invention. This invention is not limited to these examples. In these working examples were used model devices produced on a reduced scale of about 1:5 of the practical device for clinical use.

EXAMPLE 1

There was used as the test solution instead of blood a hemodialysate (AK-SOLITA made by Shimizu Pharmaceutical Co., Ltd., of Shimizu City, Japan and composed of 20.25% by weight/volume of sodium chloride, 0.522% by weight/volume of potassium chloride, 0.643% by weight/volume of calcium chloride, 0.534% by weight/volume of magnesium chloride, 15.718% by weight/volume of sodium acetate and 7% by weight/volume of glucose in a total concentration of about 6 mol/liter) diluted to 35 times the original volume and having urea, creatinine and vitamin $B_{12}$ dissolved therein in respective proportions of 105 mg/dl, 10 mg/dl and 10 mg/dl of the diluted hemodialysate as indexes of detrimental waste substances with different molecular weights.

One liter of this test solution was placed in a blood container retaining therein 50 g of spheres of activated carbon as a sorbent.

As a device for removing excess water from blood, six membranes of acetyl cellulose (a combined acetic acid of 60.5%) having a thickness of about 10 μm were fastened liquid-tightly at a fixed interval of about 200 μm in the interior of a plastic frame having an inside length of 320 mm and an inside width of 120 mm to form four high concentration solution chambers and three blood chambers. The total area of semi-permeable membranes available for the perfusion treatment was about 2300 $cm^2$, the total capacity of the blood chambers about 40 ml and that of the solution chambers about 50 ml.

As the high concentration solution, the hemodialysate which was used in the preparation of the aforementioned test solution was used in its original form.

The test solution and the high concentration solution described above were fed respectively to the blood chambers and the solution chambers. The supply of the high concentration solution was stopped by closing the pinch cock at the time that the solution overflowed all the solution chambers. The blood was continuously supplied at a fixed flow volume of 40 ml/min.

The changes in the volume of the solution flowing out of the solution outlet and the solute concentration in the test solution were measured along the course of time.

The graph of FIG. 4 shows time-course changes in the volume of excess water transferred from the test solution to the solution (Curve I) and the electroconductivity of the test solution as a measure for indirect indication of the ionic concentration in the blood (Curve II). (In view of the constancy of body fluid, any notable changes in these values is a sign of danger. The values are desired to be constant.)

In this example, the high concentration solution was not replaced. Thus, the water flux reached its saturation in a relatively short time and the volume of excess water removed amounted to about 65 ml in three hours. The initial water permeability was about $4.5 \times 10^{-4}$ ml/cm$^2$.min.

The time-course changes in the concentrations of the four components present in the test solution are shown in Table 1.

Table 1

| Solute<br>Duration of<br>treatment (min.) | Calcium<br>mg/dl | Urea<br>mg/dl | Creatinine<br>mg/dl | Vitamin B$_{12}$<br>mg/dl |
| --- | --- | --- | --- | --- |
| 0 | 4.2 | 101 | 10 | 10 |
| 35 | 4.4 | 93 | 6.4 | 6.8 |
| 95 | 4.2 | 87 | 3.6 | 3.5 |
| 155 | 4.1 | 96 | 2.0 | 2.3 |
| 215 | 4.2 | 91 | 1.4 | 1.1 |

It is seen from the table given above that after about 3.5 hours of this treatment, about 10% of urea, about 86% of creatinine, and about 89% of vitamin B$_{12}$ were removed, whereas the calcium concentration remained substantially constant. In spite of such removal of the components from the test solution, the electroconductivity of the test solution was increased by about 1 mmoh/cm$^2$ after three hours of this treatment as shown in FIG. 1. This increase in the electroconductivity corresponds to the increase in the concentration of the test solution brought about by the removal of excess water. An increase of 1 mmoh/cm$^2$ in the electroconductivity equals about 10 mEg/liter of sodium ion concentration. Since the sodium ion concentration in normal human beings is generally in the range of from 135 to 150 mEg/liter, the increase of the order mentioned is not detrimental at all. Thus, the device of this invention was demonstrated to manifest its function sufficiently for the perfusion of the blood from a patient suffering renal failure.

EXAMPLE 2

A hemodialysate was diluted to 35 times the original volume. The dilute solution has sucrose dissolved therein in a proportion of 120 g/dl so as to increase the combined concentration of contained components to about 3.7 mol/liter. The resultant solution was used as a high concentration solution. The test solution to be treated, the sorbent and the semi-permeable membranes were the same as those used in Example 1, except that the volume of the test solution used was 500 ml and the amount of the sorbent used was 25 g respectively. The sorbent was wrapped up in gauze and placed in the blood chambers as illustrated in FIG. 3. In this case, the total area of semi-permeable membranes available for the treatment was about 1900 cm$^2$, the total volume of the solution placed in the solution chambers was about 65 ml, and the flow volume of the test solution was about 50 ml/min.

After 1.5 hours and 3 hours of the treatment, the solution inside the solution chambers was replaced with a fresh supply.

Figure 5:
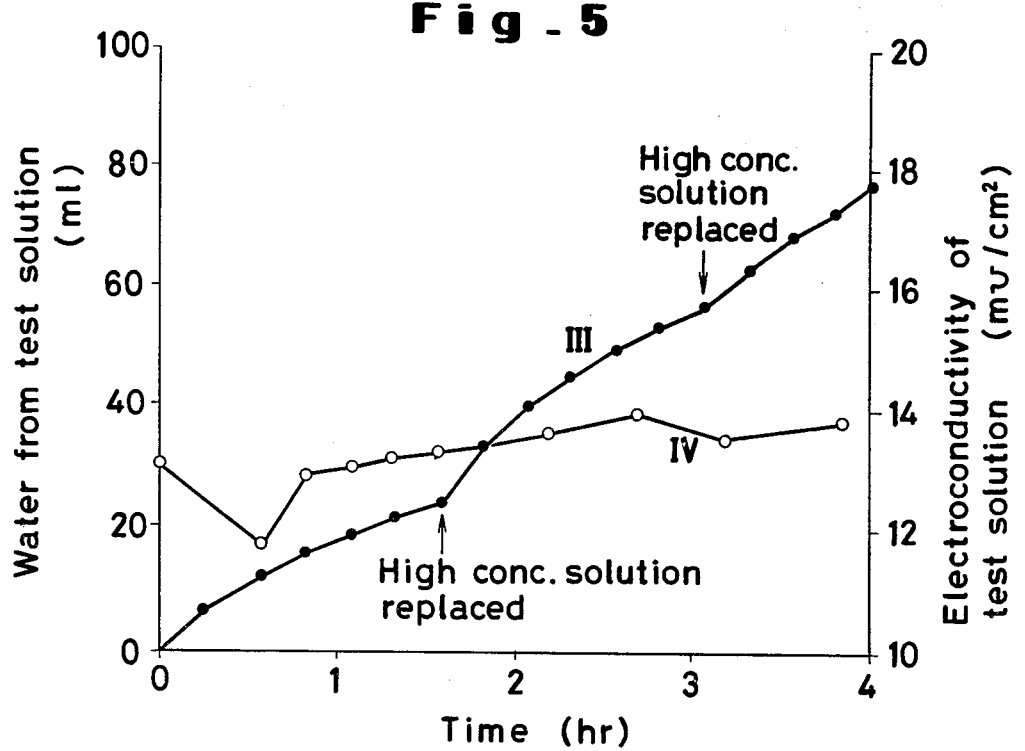

The time-course changes in the volume of excess water transferred to the solution side (Curve III) and in the electroconductivity of the test solution (Curve IV) are shown in FIG. 5. The changes in the concentrations of different solutes in the test solution after varying intervals are shown in Table 2.

Table 2

| Solute<br>Duration of<br>treatment (min.) | Calcium<br>mg/dl | Urea<br>mg/dl | Creatinine<br>mg/dl | Vitamin B$_{12}$<br>mg/dl |
| --- | --- | --- | --- | --- |
| 0 | 4.2 | 103 | 9.7 | 10 |
| 35 | 4.4 | 96 | 7.0 | 9.0 |
| 95 | 4.4 | 92 | 5.3 | 6.7 |
| 162 | 4.4 | 93 | 4.2 | 5.4 |
| 232 | 4.1 | 92 | 3.3 | 4.3 |

Since the solution used in this example had a concentration about one half that of the solution used in Example 1, the initial water flux was $2.1 \times 10^{-4}$ ml/cm$^2$/min, a value about half as small. Since the solution was replaced with a fresh supply at the time that its water permeating capacity reached saturation as shown in FIG. 5, the solution could retain its water flux virtually constant. After four hours of treatment, the volume of excess water removed reached about 80 ml.

The changes in the concentrations of the individual solutes in the test solution were almost the same as those obtained in Example 1, as shown in Table 2, and the calcium concentration remained substantially constant.

As shown in FIG. 5, the electroconductivity of the test solution showed a slight increase. In consideration of the fact that the volume of the test solution used was one half that of Example 1, the increase of this order is not believed to bring about any detrimental effect on the actual operation of the device of this invention.

What is claimed is:

1. A device for the removal of excess water contained in the blood by utilization of osmotic pressure, which device comprises in combination:

a plurality of solution chambers possessed of one feed inlet connected to all of said solution chambers, said feed inlet having a pinch cock, and one constantly open discharge outlet connected to all of said solution chambers;

water suction means disposed inside said plurality of solution chambers for removing the excess water in the blood, said water suction means being a high concentration solution containing a concentration of 3.7-6 mol/liter solutes comprising calcium chloride, and one from the group consisting of glucose and sucrose, said pinch cock permitting the passage of a fresh high concentration solution through said feed inlet into said plurality of solution chambers and thereby allowing the discharge of said high concentration solution in said plurality of solution chambers out of said discharge outlet when said pinch cock is opened;

a plurality of blood chambers allowing the blood subjected to perfusion treatment to pass therethrough, said solution chambers and said blood chambers being alternately disposed; and a plurality of normal osmotic semi-permeable membranes inserted to partition the adjoining ones of the alternately disposed chambers, said semipermeable membranes exhibiting solute permeability for said solutions in the range of from $1 \times 10^{-7}$ cm/min. to $7 \times 10^{-6}$ cm/min. at the time said semi-permeable membranes have come into contact with said high concentration solution at one side thereof and with the blood at the other side thereof, whereby the excess water contained in the blood is allowed to pass through said semi-permeable membranes by osmotic pressure into said solution chambers and said solutes contained in said high concentration solution are prevented from passing through said semi-permeable membranes into said blood chambers.

2. The device according to claim 1, wherein the blood chambers retain therein a sorbent wrapped up in a liquid-previous substance.

3. The device according to claim 2, wherein the sorbent is in the form of spheres of activated carbon.

4. The device according to claim 1, which further comprises means for supplying to said blood chambers blood which has been treated in advance with a sorbent.

5. The device according to claim 1, which further comprises means for treating blood with a sorbent after the blood has passed through said blood chambers.

6. The device according to claim 1, wherein said semi-permeable membranes are made of acetyl cellulose with a degree of acetylation of 60.5%.

* * * * *